US012642424B2

(12) United States Patent
Shirazian et al.

(10) Patent No.: US 12,642,424 B2
(45) Date of Patent: Jun. 2, 2026

(54) SYSTEMS AND METHODS FOR A DIFFERENTIATED INTERACTION ENVIRONMENT

(71) Applicant: INTUITIVE SURGICAL OPERATIONS, INC., Sunnyvale, CA (US)

(72) Inventors: Pourya Shirazian, Menlo Park, CA (US); Daniel Proksch, San Jose, CA (US); Erik D. Wakefield, Issaquah, WA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 232 days.

(21) Appl. No.: 18/681,005

(22) PCT Filed: Aug. 9, 2022

(86) PCT No.: PCT/US2022/039786
§ 371 (c)(1),
(2) Date: Feb. 2, 2024

(87) PCT Pub. No.: WO2023/018685
PCT Pub. Date: Feb. 16, 2023

(65) Prior Publication Data
US 2025/0120569 A1     Apr. 17, 2025

Related U.S. Application Data

(60) Provisional application No. 63/303,101, filed on Jan. 26, 2022, provisional application No. 63/231,658, filed on Aug. 10, 2021.

(51) Int. Cl.
*G06T 19/00* (2011.01)
*A61B 1/00* (2006.01)
(Continued)

(52) U.S. Cl.
CPC ............ *A61B 1/0005* (2013.01); *G06T 15/20* (2013.01); *G06T 17/20* (2013.01); *G06T 19/006* (2013.01);
(Continued)

(58) Field of Classification Search
None
See application file for complete search history.

(56) References Cited

U.S. PATENT DOCUMENTS

2003/0197781 A1* 10/2003 Sugimoto .............. H04N 7/181
600/172
2009/0248036 A1* 10/2009 Hoffman ............ A61B 1/00149
606/130

(Continued)

OTHER PUBLICATIONS

International Search Report and Written Opinion for Application No. PCT/US2022/039786, mailed Dec. 6, 2022, 12 pages.
(Continued)

*Primary Examiner* — Nicholas R Wilson
(74) *Attorney, Agent, or Firm* — Haynes & Boone, LLP

(57) ABSTRACT
A system comprises a processor and a memory having computer readable instructions stored thereon. The computer readable instructions, when executed by the processor, cause the system to generate a current endoscopic video image of a surgical environment, capture an image from the current endoscopic video image, display the current endoscopic video image and the captured image in a common display, and perform an action with the captured image in response to a user input.

20 Claims, 4 Drawing Sheets

200

202 — GENERATE AN ENDOSCOPIC VIDEO IMAGE

204 — CAPTURE AN IMAGE FROM THE ENDOSCOPIC VIDEO IMAGE

206 — DISPLAY THE ENDOSCOPIC VIDEO IMAGE AND THE CAPTURED IMAGE ON A COMMON DISPLAY

208 — PERFORM AN ACTION WITH THE CAPTURED IMAGE

(51) Int. Cl.
  _G06T 15/20_      (2011.01)
  _G06T 17/20_      (2006.01)
(52) U.S. Cl.
  CPC ...... _G06T 2210/41_ (2013.01); _G06T 2210/56_
         (2013.01); _G06T 2219/012_ (2013.01)

(56)              References Cited

U.S. PATENT DOCUMENTS

| | | | |
|---|---|---|---|
| 2016/0210411 A1* | 7/2016 | Mentis | G06F 3/0304 |
| 2016/0287141 A1* | 10/2016 | Sidlesky | G02B 23/2415 |
| 2019/0133418 A1* | 5/2019 | Furuhata | A61B 1/00096 |
| 2019/0297276 A1* | 9/2019 | Sachdev | G16H 30/40 |
| 2020/0125236 A1* | 4/2020 | Palushi | G06F 3/04812 |
| 2021/0233298 A1 | 7/2021 | Usuda | |

OTHER PUBLICATIONS

Vertut, J., and Coiffet, P., "Robot Technology: Teleoperation and
Robotics Evolution and Development," English translation, Prentice-
Hall, Inc., Inglewood Cliffs, NJ, USA 1986, vol. 3A, 332 pages.
International Preliminary Report on Patentability for Application
No. PCT/US2022/039786, mailed Feb. 22, 2024, 07 pages.

* cited by examiner

200

202 — GENERATE AN ENDOSCOPIC VIDEO IMAGE

204 — CAPTURE AN IMAGE FROM THE ENDOSCOPIC VIDEO IMAGE

206 — DISPLAY THE ENDOSCOPIC VIDEO IMAGE AND THE CAPTURED IMAGE ON A COMMON DISPLAY

208 — PERFORM AN ACTION WITH THE CAPTURED IMAGE

250

252

260

280

SYSTEMS AND METHODS FOR A DIFFERENTIATED INTERACTION ENVIRONMENT

CROSS-REFERENCED APPLICATIONS

This application is the U.S. national phase of International Application No. PCT/US2022/039786, filed Aug. 9, 2022, which designated the U.S. and claims priority to and the benefit of U.S. Provisional Application No. 63/303,101 filed Jan. 26, 2022, and of U.S. Provisional Application No. 63/231,658, filed Aug. 10, 2021, both entitled "Systems and Methods for a Differentiated Interaction Environment," all of which are incorporated by reference herein in their entirety.

FIELD

The present disclosure is directed to systems and methods for providing a displayed interaction environment distinct from a displayed clinical environment.

BACKGROUND

Minimally invasive medical techniques are intended to reduce the amount of tissue that is damaged during diagnostic or surgical procedures, thereby reducing patient recovery time, discomfort, and harmful side effects. Such minimally invasive techniques may be performed through one or more surgical incisions or through natural orifices in a patient anatomy. Through these incisions or natural orifices, clinicians may insert minimally invasive medical instruments, including endoscopic imaging systems to capture images of tissue within the patient anatomy. The endoscopic imaging systems may be three-dimensional imaging systems that provide a three-dimensional video image of the tissue. Systems and methods are needed for displaying the video image of the tissue while also providing a differentiated, displayed interaction environment for interacting with a captured image from the video image.

SUMMARY

Examples of the invention are summarized by the claims that follow the description. Consistent with some examples, a system may comprise a processor and a memory having computer readable instructions stored thereon. The computer readable instructions, when executed by the processor, cause the system to generate a current endoscopic video image of a surgical environment, capture an image from the current endoscopic video image, display the current endoscopic video image and the captured image in a common display, and perform an action with the captured image in response to a user input.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
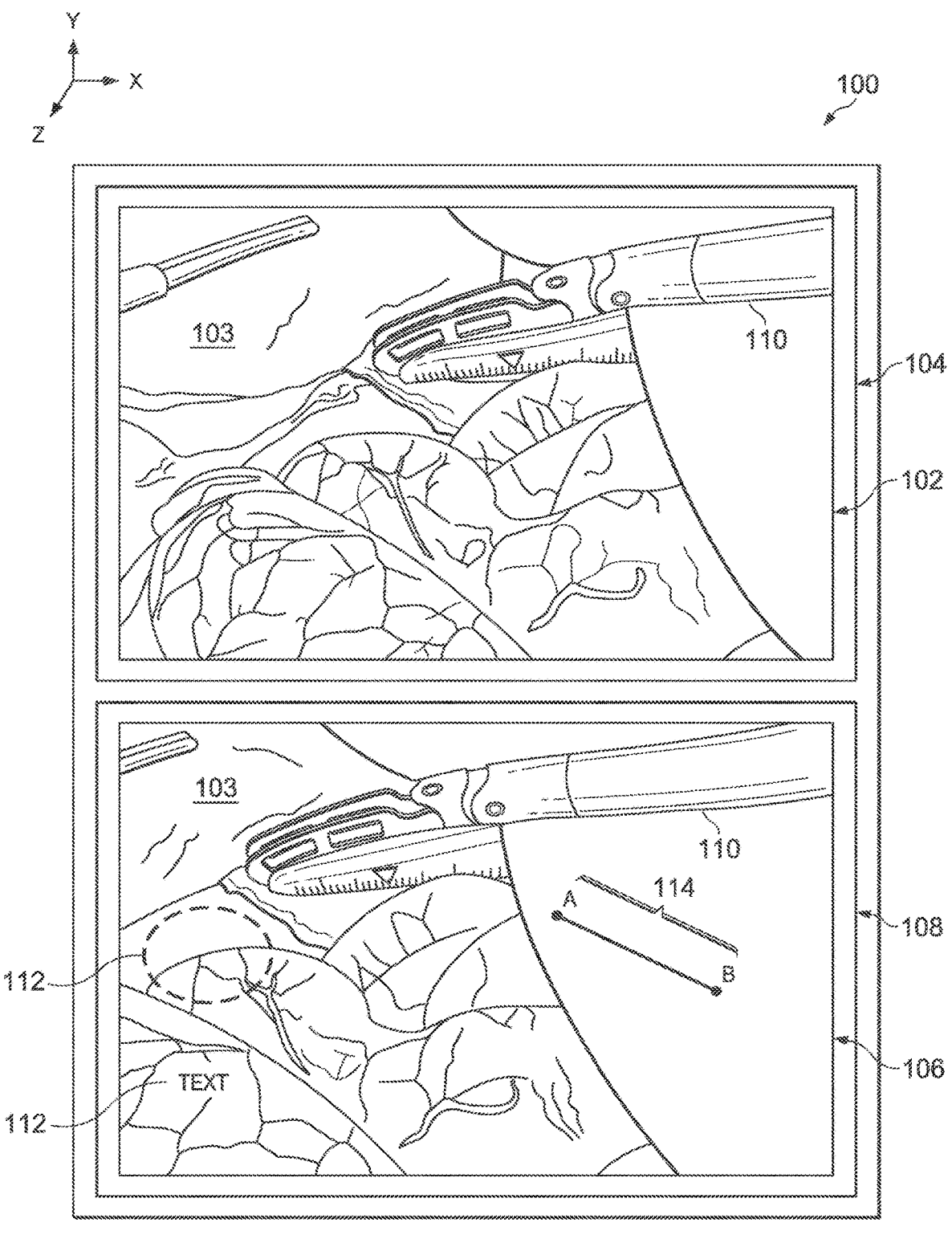
FIG. 1 illustrates a display system displaying an endoscopic video image and an image captured from the endoscopic video image, according to some embodiments.

Embodiments of the present disclosure and their advantages are best understood by referring to the detailed description that follows. It should be appreciated that like reference numerals are used to identify like elements illustrated in one or more of the figures for purposes of illustrating but not limiting embodiments of the present disclosure.

DETAILED DESCRIPTION

Systems and methods are provided for displaying a surgical environment, in which clinical interactions with patient tissue occur, and a differentiated interaction environment that allows for interaction with a captured image of the surgical environment in response to a user input.

Figure 4:
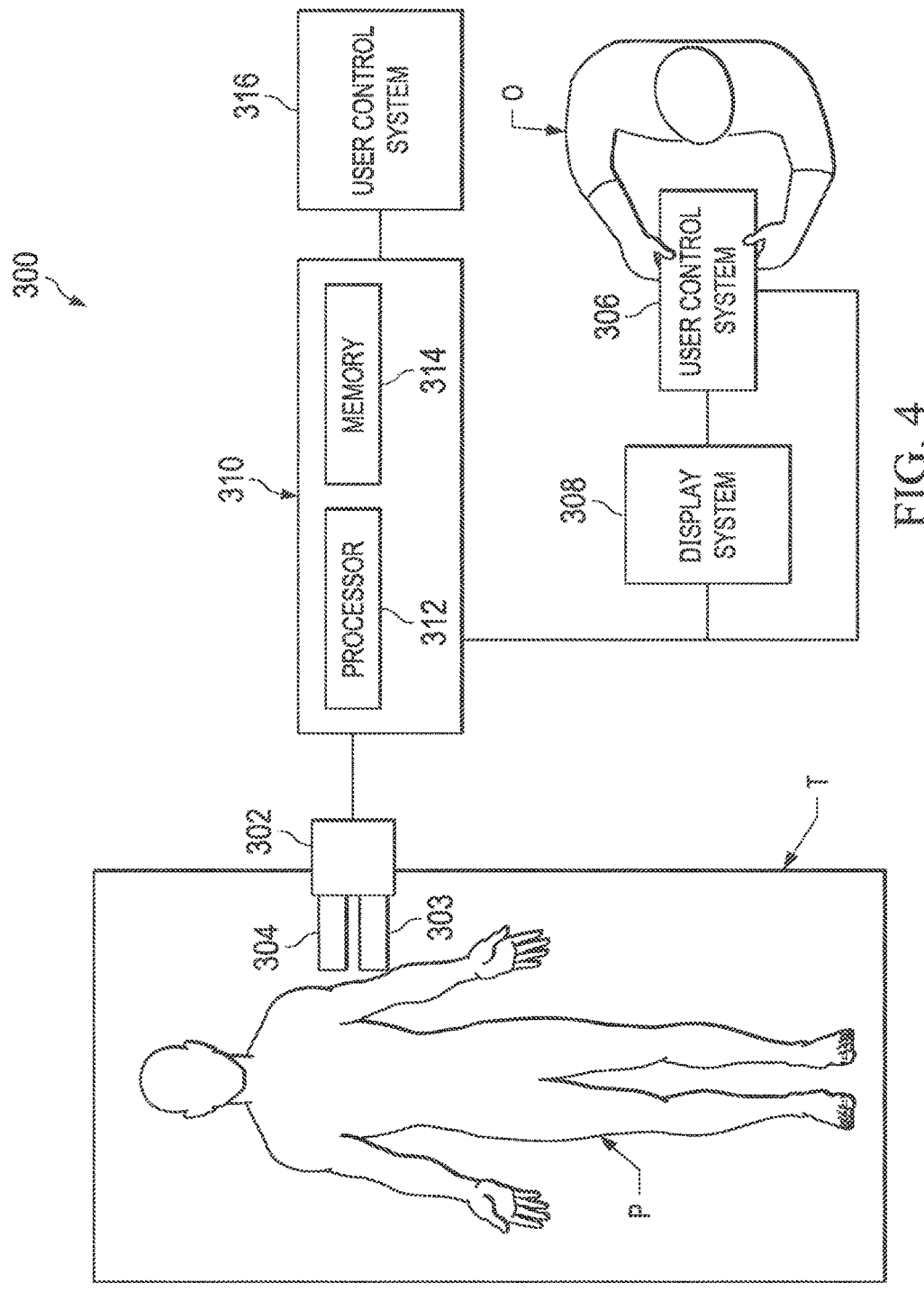
FIG. 4 is a simplified diagram of a robotically-assisted medical system according to some embodiments.

FIG. 1 illustrates a display system 100 displaying a current endoscopic video image 102 of a surgical environment 103 in a first window 104 and a captured image 106 of the surgical environment 103 in a second window 108. The display system 100 may be part of a robotically-assisted medical system (e.g. a display system 308 of a medical system 300 as shown in FIG. 4) that controls a medical instrument 110 in the surgical environment 103 during a medical procedure. The current endoscopic video image 102 may be a two or three-dimensional live video image generated by an endoscopic imaging system (e.g., imaging system 304 of the medical system 300 as shown in FIG. 4) positioned in the surgical environment. The captured image 106 may be a still or frozen image captured or recorded by the endoscopic imaging system during the medical procedure. For example, the captured image 106 may be a still image captured from the endoscopic video image at a time prior to the current endoscopic video image 102. Thus, the first window 104 may display the current endoscopic video image 102 while the second window 108 may display an image 106 captured at a time prior to the current endoscopic video image 102. Because the current endoscopic video image 102 may display a live image of the surgical environment, the position and orientation of the medical instrument 110 or other equipment in the current endoscopic video image 102 may be different from the position and orientation of the medical instrument 110 in the captured image 106 because the medical instrument 110 may have been moved since the captured image 106 was recorded. Similarly, the position and orientation of patient tissue in the current endoscopic video image 102 may be different from the position and orientation of the patient tissue in the captured image 106 because the patient tissue may have moved due to a surgical intervention or patient motion such as respiration. Additionally or alternatively, the position and orientations of medical instruments and/or patient tissue may appear in different positions in the captured image 106 because the position of the imaging system may have changed since the image 106 was recorded. In some examples, the captured image 106 may be a video image (rather than a still image) captured or recorded by the endoscopic imaging system during the medical procedure prior to the video image 102.

In the example of FIG. 1, the window 104 is positioned above the window 108, but in alternative examples, the positions of the windows may be swapped, or the windows may be arranged side by side (e.g., left and right). In some examples, the position or size of the windows may be changeable by the user. In some examples, the position or size of the windows may change based on the operating mode of the robotically-assisted medical system. For example, the window 104 may be larger than the window 108 when in an instrument following mode of the robotically-assisted medical system in which the instrument 110 is under active control of a user input device (e.g., a user interface device of user control system 306 of a medical system 300 as shown in FIG. 4). The second window may be larger than the first window when in an image control mode of the robotically-assisted medical system in which user input device does not actively control the instrument 110 but instead actively controls a cursor or other user interface element.

Figures 2, 3A:
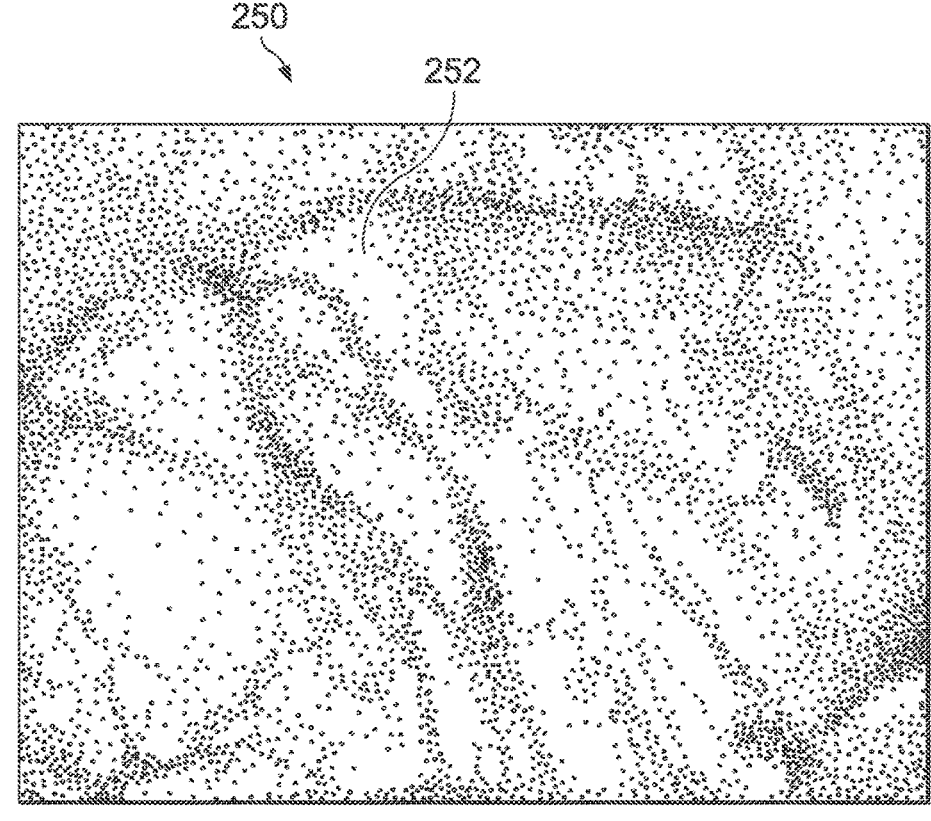
FIG. 2 is a flowchart illustrating a method for differentiated interaction environment, according to some embodiments.
FIG. 3A illustrates an augmented captured image, according to some embodiments.

FIG. 2 is a flowchart illustrating a method 200 for generating an augmented or mixed-reality image, according to some embodiments. The method 200 is illustrated as a set of operations or processes. The processes illustrated in FIG. 2 may be performed in a different order than the order shown in FIG. 2, and one or more of the illustrated processes might not be performed in some embodiments of method 200. Additionally, one or more processes that are not expressly illustrated in FIG. 2 may be included before, after, in between, or as part of the illustrated processes. In some embodiments, one or more of the processes of method 200 may be implemented, at least in part, in the form of executable code stored on non-transitory, tangible, machine-readable media that when run by one or more processors (e.g., the processors of a control system) may cause the one or more processors to perform one or more of the processes.

At a process 202, an image (e.g. endoscopic image 102) may be generated by an imaging system (e.g., an endoscopic imaging system 304). The endoscopic image may be generated from a live three-dimensional video of the surgical environment captured by the endoscopic imaging system. The image may be a two or three-dimensional live video or still image generated by an imaging system currently within a patient anatomy.

At a process 204, an image (e.g. image 106) may be captured from the endoscopic video image. The captured image may be a still or frozen image captured or recorded by the imaging system during the medical procedure in which the live image of process 202 was generated. For example, the captured image 106 may be a still image captured from the endoscopic video image at a time prior to the current endoscopic video image 102.

At a process 206, the endoscopic video image and the captured image may be displayed on a common display system (e.g. display system 100). For example, the first window 104 on display system 100 may display the current endoscopic video image 102 while the second window 108 may display the image 106 captured at a time prior to the current endoscopic video image 102.

At a process 208, an action may be performed with the captured image. For example, an interaction may be performed with the captured image 106 in response to a user input. The interaction may be a telestration that displays with the captured image, a virtual movement or rotation of the captured image, a measurement of structures or instruments in the surgical environment, or other interactions that assist with performing the medical procedure. The action may also or alternatively include augmenting or modifying the captured image to create an augmented or mixed-reality image displayed in the window 108.

Optionally, in some embodiments, a following mode of a robotically-assisted medical system may be suspended and an image control mode of the robotically-assisted medical system may be entered before performing the action with the captured image at process 208. In following mode, the movement of the medical instrument 110 in the surgical environment 103 is responsive to movement of the user input device. In the image control mode, the movement of a medical instrument in the surgical environment is not responsive to movement of the user input device. In some examples, in the image control mode, the user input device that is used to move the medical instrument (in the following mode) may instead be used to perform the interaction with the captured image. For example, a six degree of freedom user input device may be restricted to movement in two dimensions that are registered to the captured image to control a cursor, selector, keyboard, menu, or other user interface associated with the captured image. In some examples, in the image control mode, a second user input device, different from the user input device that is used to move the medical instrument (in the following mode), may be used to perform the interaction with the captured image. The second user input device may be part of the user console or may be at a second surgical console, a computer, a tablet, or other device controlled by the clinician or by a second user.

Optionally, in some embodiments, a following mode of a robotically-assisted medical system may not be suspended before performing the action with the captured image at process 208. In this embodiment, movement of the medical instrument 110 in the surgical environment 103 remains responsive to movement of the user input device, and the second user input device, different from the first user input device used to move the medical instrument in the following mode, may instead be used to perform the interaction with the captured image.

Various actions can be performed with the captured image 106 displayed in the window 108 in response to a user input at a user control system (e.g., user control system 306 in FIG. 4). For example, the action performed may be displaying a telestration 112 generated in response to the user input. Telestrations may include numerical or textual characters, freehand drawings, symbols, shapes, arrows, or other notes or annotations superimposed on or around the captured image. These telestrations may provide communication with other viewers of the captured image such and surgical staff, students, or supervisors, or the telestrations may be useful to the clinician generating the telestrations to provide reminders, guidance, or additional information. The telestrations may be generated by the operator of the medical instrument 110 or may be generated by a different user. In some examples, the telestrations may be generated by keyboard user input device to generate textual annotations that reference the scene in the captured image 106. In some examples, the telestrations may be generated by moving a multiple-degree of freedom user input device to generate free-hand shape or select annotation choices from a menu. In some examples, the telestrations or other markings made by the operator or another clinician may be saved and retrieved for later viewing in the captured image in the window 108.

In some examples, the action performed with the captured image in response to the user input may be measurement of structures or distances in the surgical environment 103. For example, points A and B may be marked on captured image 106 by the user input device, and a linear or curvilinear distance 114 between the points may be calculated based on the two-dimensional (X-Y dimensions) scale of the image 106 and optionally based on a depth map (Z-dimension) that provides the distance between the distal end of the endoscope and the tissue surface at each pixel in the image. In some examples, a ventral hernia site may be measured to select an appropriate size for a mesh application.

In some examples, the action performed with the captured image in response to the user input may be altering a virtual viewpoint of a virtual camera. The virtual camera for generating a virtual camera image may be generated based on intrinsic and extrinsic parameters of the endoscope calibration data. The virtual camera may mimic the behavior of the endoscope (e.g., image capturing device 304), allowing an area within the patient anatomy (e.g., an interventional area or a surgical environment) to be viewed from camera angles or positions different from the position and/or orientation of the live endoscopic view from the endoscope (e.g., image capturing device 304) physically positioned within the patient anatomy. The virtual camera may have the same calibration parameters as the endoscope. The virtual camera may allow a viewer to observe and analyze the size, volumes, and spatial relationships of anatomic structures, suspicious masses, other instruments, or any other objects in the anatomic area from different viewpoints.

In some examples when the captured image is displayed on a common display system (e.g., at process 206), the displayed captured image may be an augmented captured image. For example, the captured image 106 is may be differentiated from the displayed current endoscopic video image 102 by a graphical indicator, treatment, or image augmentation which may include, for example, a grayscale presentation of the captured image, a color modification of the captured image, a grid projection on the captured image, and/or a textual, graphical, or numerical marking on or adjacent to the captured image. In some examples, as shown in FIG. 3A, an augmented captured image 250 may be generated using a depth-map visualization to display as the augmented captured image 106. To generate the depth-map visualization, a depth-map point-cloud 252 may be computed from a captured stereo-endoscopic image (e.g., an image captured from the current image 102). The depth-map point cloud 252 may be rendered in the captured image window 108 and displayed as the augmented captured image 106. Alternatively, the depth-map point cloud 252 may be merged with the captured image, superimposed on the captured image, or otherwise displayed with the captured image. The depth-map may be generated from a disparity map that maps the difference between pixel locations between a pair of stereo images. The disparity is the relative distance between an image feature, such as a pixel. From the known disparity, a known baseline distance between the two camera lenses, and a known local length of the lenses, a depth for each pixel or feature may be determined and mapped. The depth map may be used to convert the captured image to a point cloud of pixels in a three dimensional image. Converting the depth map to a point cloud allows for the performance of point cloud specific operations. For example, a point cloud of an intra-operative captured image may be registered to a point cloud of a pre-operative image. In some examples, a point cloud may be subsampled to remove noise and perform feature detection. A point cloud may also be used to generate a 3D surface model of structures in a captured image.

Figure 3B:
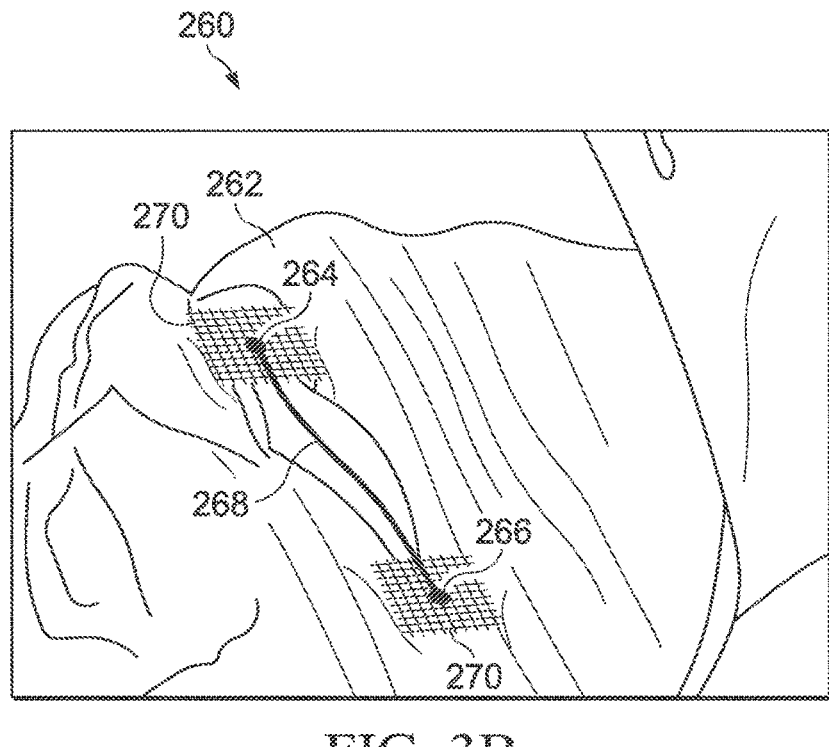
FIG. 3B illustrates an augmented captured image, according to some embodiments.

In some examples, as shown in FIG. 3B, an augmented captured image 260 may be generated using a localized mesh visualization around endpoints of a two or three-dimensional ruler. In this example, the mixed-reality image 260 may be created from a captured stereo-endoscopic image 262 (e.g., an image captured from the current image 102). Endpoints 264, 266 of a ruler or measuring device 268 may be marked on the image 262. A mesh 270 reconstructed from a depth-map point-cloud may be rendered at the ruler endpoints 264, 266. For example, in anatomical areas with sharp curves, an operator may observe a virtual view of the anatomy from a slightly perturbed orientation to better reveal anatomic features not visible in the live image. When performing a measurement, the altered or perturbed view may help the operator understand the curvature of the anatomic surface.

Figure 3C:
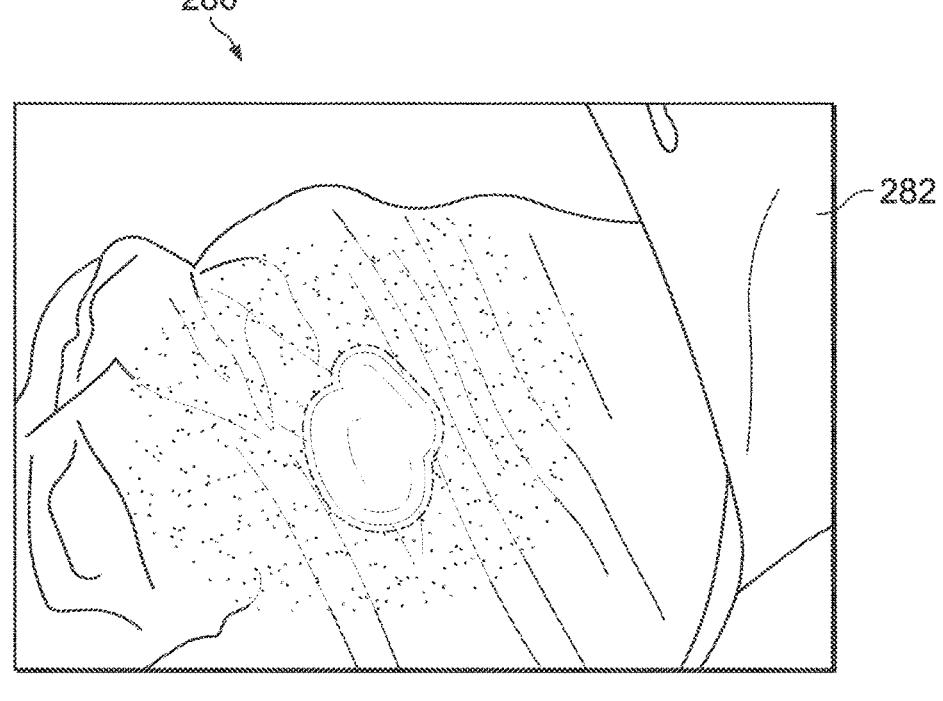
FIG. 3C illustrates an augmented captured image, according to some embodiments.

In some examples, as shown in FIG. 3C, an augmented captured image 280 may be generated using a cut through visualization with a slope image. In this example, the mixed-reality image 280 may be created from a captured stereo-endoscopic image 282 (e.g. an image captured from the current image 102) augmented to include a cut-through view to a pre-operative segmented model of a structure 284, such as a tumor, that is located below the surface of the tissue. The augmented image 280 may be the product of three blended images including a stereo endoscopic image, a slope image generated from the stereo endoscopic image as described below, and a pre-operative segmented model captured with an imaging modality such as CT or MR. To create the cut through visualization from the slope image, an intensity image may be computed first from an endoscopic color image. The horizontal and vertical components of an image gradient, g0 and g1, may be computed using a Sobel filter from the intensity image. Per each pixel, the surface slope components p and q may be computed across the X and Y directions, respectively. The X and Y coordinates may be the normalized coordinates of an output image pixel. The values, g0 and g1, may be the surface gradient along the X and Y directions, respectively. The value e is an epsilon value that may be set to 0.00001 in some examples. The slope is the final image slope at a pixel.

$$p = \left(-g0\,x^2 - g0y^2 - g0 - 3\ e\ x\right)/$$
$$\left(-g0\,x^3 - g0 \times y^2 - g0\,x - g1\,x^2\,y - g1\,y^3 - g1\,y + 3\,e\right)$$
$$q = \left(g1\,x^2 + g1\,y^2 + g1 + 3\ e\ y\right)/$$
$$\left(g0\,x^3 + g0\,x\,y^2 + g0\,x + g1\,x^2\,y + g1\,y^3 + g1\,y - 3\,e\right)$$
$$slope = \log(abs(p) + abs(q))$$

A gaussian filter may be applied to the slope image to smooth the rough edges. The slope image may be blended with the color image and the image of the pre-operative segmented model for a differentiated visualization 400 as shown in FIG. 3C.

The systems and methods described herein may be implemented with a robotically-assisted medical system that includes an endoscopic imaging system, user input devices for identifying the surface points, and a display system for displaying the rendered endoscopic and mixed-reality images. FIG. 4 is a simplified diagram of a robotically-assisted medical system 300 that may be used with the systems and methods described herein. In some embodiments, system 300 may be suitable for use in therapeutic, diagnostic, and/or imaging procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems. For example, the systems, instruments, and methods described herein may be used for non-medical purposes including industrial uses, general robotic uses, and manipulating non-tissue work pieces.

As shown in FIG. 4, system 300 generally includes a manipulator assembly 302. The manipulator assembly 302 is used to operate a medical instrument 303 (e.g., a surgical instrument) and medical instrument 304 (e.g., an image capturing device) in performing various procedures on a patient P. The manipulator assembly 302 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 302 is mounted to or located near an operating or surgical table T.

A user control system 306 allows an operator O (e.g., a surgeon or other clinician as illustrated in FIG. 4) to view the interventional site and to control manipulator assembly 302. In some examples, the user control system 306 is a surgeon console, which is usually located in the same room as the operating or surgical table T, such as at the side of a table on which patient P is located. It is to be understood, however, that operator O can be located in a different room or a completely different building from patient P. That is, one or more user control systems 306 may be collocated with the manipulator assemblies 302, or the user control systems may be positioned in separate locations. Multiple user control systems allow more than one operator to control one or more robotically-assisted manipulator assemblies in various combinations.

User control system 306 generally includes one or more input devices for controlling manipulator assembly 302. The input devices may include any number of a variety of devices, such as a keyboard, joysticks, trackballs, data gloves, trigger-guns, hand-operated controllers, voice recognition devices, body motion or presence sensors, and/or the like. To provide operator O with a strong sense of directly controlling medical instruments 303,304, the input devices may be provided with the same degrees of freedom as the associated medical instruments 303, 304. In this manner, the input devices provide operator O with telepresence and the perception that the input devices are integral with medical instruments 303, 304. Optionally, the system 300 may also include a second user control system 316 with a second user input device. The second input devices may include any number of a variety of devices, such as a keyboard, joysticks, trackballs, data gloves, trigger-guns, hand-operated controllers, voice recognition devices, body motion or presence sensors, and/or the like. The second user control system 316 may be under the control of the operator O or another user for interacting with the captured image.

Manipulator assembly 302 supports medical instruments 303, 304 and may include a kinematic manipulator support structure of one or more non-servo controlled linkages (e.g., one or more links that may be manually positioned and locked in place), and/or one or more servo controlled linkages (e.g., one or more links that may be controlled in response to commands from a control system), and an instrument holder. Manipulator assembly 302 may optionally include a plurality of actuators or motors that drive inputs on medical instruments 303, 304 in response to commands from the control system (e.g., a control system 310). The actuators may optionally include drive systems that when coupled to medical instruments 303, 304 may advance medical instruments 303, 304 into a naturally or surgically created anatomic orifice. Other drive systems may move the distal end of medical instruments 303, 304 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the actuators can be used to actuate an articulable end effector of medical instrument 303 for grasping tissue in the jaws of a biopsy device and/or the like. Actuator position sensors such as resolvers, encoders, potentiometers, and other mechanisms may provide sensor data to system 300 describing the rotation and orientation of the motor shafts. This position sensor data may be used to determine motion of the objects manipulated by the actuators. The manipulator assembly 302 may position its held instruments 303, 304 so that a pivot point occurs at the instrument's entry aperture into the patient. The pivot point may be referred to as a remote center of manipulation. The manipulator assembly 302 may then manipulate its held instrument so that the instrument may be pivoted about the remote center of manipulation, inserted into and retracted out of the entry aperture, and rotated about its shaft axis.

System 300 also includes a display system 308 for displaying an image or representation of the surgical site and medical instrument 303 generated by the instrument 304. Display system 308 and user control system 306 may be oriented so operator O can control medical instruments 303, 304 and user control system 306 with the perception of telepresence. In some examples, the display system 308 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

System 300 also includes control system 310. Control system 310 includes at least one memory 314 and at least one computer processor 312 for effecting control between medical instruments 303, 304, user control system 306, and display system 308. Control system 310 also includes programmed instructions (e.g., a non-transitory machine-readable medium storing the instructions) to implement some or all of the methods described in accordance with aspects disclosed herein, including instructions for providing information to display system 308. While control system 310 is shown as a single block in the simplified schematic of FIG. 4, the system may include two or more data processing circuits with one portion of the processing optionally being performed on or adjacent to manipulator assembly 302, another portion of the processing being performed at user control system 306, and/or the like. The processors of control system 310 may execute instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, control system 310 supports wireless communication protocols such as Bluetooth, IrDA, HomeRF, IEEE 802.11, DECT, and Wireless Telemetry.

Movement of a manipulator assembly 302 may be controlled by the control system 310 so that a shaft or intermediate portion of instruments mounted to the manipulator assemblies 302 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, excessive lateral motion of the shaft that might otherwise tear the tissues adjacent the aperture or enlarge the access site inadvertently is inhibited. Some or all of such constraint on the motions of the manipulator assemblies 302 at the access sites may be imposed using mechanical manipulator joint linkages that inhibit improper motions or may in part or in full be imposed using data processing and control techniques. In some embodiments, control system 310 may receive force and/or torque feedback from medical instrument 304. Responsive to the feedback, control system 310 may transmit signals to user control system 306. In some examples, control system 310 may transmit signals instructing one or more actuators of manipulator assembly 302 to move medical instruments 303, 304.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Not all the illustrated processes may be performed in all embodiments of the disclosed methods. Additionally, one or more processes that are not expressly illustrated in may be included before, after, in between, or as part of the illustrated processes. In some embodiments, one or more of the processes may be performed by a control system or may be implemented, at least in part, in the form of executable code stored on non-transitory, tangible, machine-readable media that when run by one or more processors may cause the one or more processors to perform one or more of the processes.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for imaging, any of a variety of anatomic systems, including the lung, colon, the intestines, the stomach, the liver, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented might not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term position refers to the location of an object or a portion of an object in a three-dimensional space (e.g., three degrees of translational freedom along Cartesian x-, y-, and z-coordinates). As used herein, the term orientation refers to the rotational placement of an object or a portion of an object (e.g., in one or more degrees of rotational freedom such as roll, pitch, and/or yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

While certain illustrative embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a processor; and
a memory having computer readable instructions stored thereon, the computer readable instructions, when executed by the processor, cause the system to:
generate a current endoscopic video image of a surgical environment;
capture an image from the current endoscopic video image;
display the current endoscopic video image and the captured image simultaneously;
perform an action with the captured image in response to a user input; and
suspend a following mode of a robotically-assisted medical system and enter an image control mode before performing the action with the captured image.

2. The system of claim 1 wherein both the displayed current endoscopic video image and the captured image include an image of a medical instrument and patient tissue, wherein the medical instrument is positioned in a first position relative to the patient tissue in the captured image and in a second position, different from the first position, in the current endoscopic video image.

3. The system of claim 1, wherein the captured image is a still image.

4. The system of claim 1, wherein the captured image is a video image.

5. The system of claim 1, wherein the displayed endoscopic video image is displayed in a first window and the displayed captured image is displayed in a second window, wherein the first and second windows are adjacent to each other.

6. The system of claim 1, wherein the action is displaying a telestration generated in response to the user input.

7. The system of claim 1, wherein the action is measuring a dimension between two points in the captured image.

8. The system of claim 7, wherein the two points are generated in response to the user input.

9. The system of claim 1, wherein the action is altering a virtual viewpoint of a virtual camera.

10. The system of claim 1, further comprising a user input device wherein movement of a medical instrument in the surgical environment is responsive to movement of the user input device while in the following mode and wherein movement of the medical instrument in the surgical environment is not responsive to movement of the user input device while in the image control mode.

11. The system of claim 1, further comprising a first user input device wherein movement of a medical instrument in the surgical environment is responsive to movement of the first user input device and further comprising a second user input device wherein performing the action with the captured image is in response to the user input at the second user input device.

12. The system of claim 1, wherein the captured image is captured at a first time and the current endoscopic video image and the captured image are displayed at a second time, later than the first time.

13. The system of claim 1, wherein the captured image:
is augmented by application of a mesh graphic over at least a part of the captured image;
is augmented with a depth-map point cloud;
is augmented with a cut through visualization including a slope image; or
is augmented with text or marking.

14. The system of claim 1, wherein the current endoscopic video image and the captured image are displayed simultaneously in a common display.

15. A non-transitory machine-readable media storing instructions that, when run by one or more processors, cause the one or more processors to:
generate a current endoscopic video image of a surgical environment;
capture an image from the current endoscopic video image;
simultaneously display the current endoscopic video image and the captured image;
perform an action with the captured image in response to a user input; and
suspend a following mode of a robotically-assisted medical system and enter an image control mode before performing the action with the captured image.

16. The non-transitory machine-readable media of claim 15 wherein both the displayed endoscopic video image and the captured image include an image of a medical instrument and patient tissue, wherein the medical instrument is positioned in a first position relative to the patient tissue in the captured image and in a second position, different from the first position, in the endoscopic video image.

17. The non-transitory machine-readable media of claim 15, wherein the displayed endoscopic video image is displayed in a first window and the displayed captured image is displayed in a second window, wherein the first and second windows are adjacent to each other.

18. The non-transitory machine-readable media of claim 15, wherein the current endoscopic video image and the captured image are displayed simultaneously in a common display.

19. The non-transitory machine-readable media of claim 15, wherein the instructions further cause the one or more processors to control movement of a medical instrument in the surgical environment in response to movement of a user input device while in the following mode and not control movement of the medical instrument in the surgical environment in response to movement of the user input device while in the image control mode.

20. The non-transitory machine-readable media of claim 15, wherein the instructions further cause the one or more processors to control movement of a medical instrument in the surgical environment in response to movement of a first user input device and wherein performing the action with the captured image is in response to the user input at a second user input device.

\* \* \* \* \*